(12) United States Patent
Vanhelmont et al.

(10) Patent No.: US 11,774,389 B2
(45) Date of Patent: Oct. 3, 2023

(54) MONOLITHIC SENSOR ARRANGEMENT, MANUFACTURING METHOD AND MEASUREMENT METHOD

(71) Applicant: Sciosense B.V., AE Eindhoven (NL)

(72) Inventors: Frederik Willem Maurits Vanhelmont, Maaseik (BE); Nebojsa Nenadovic, Wijchen (NL); Hilco Suy, Son en Breugel (NL); Hooman Habibi, Eindhoven (NL)

(73) Assignee: Sciosense B.V., AE Eindhoven (NL)

( * ) Notice: Subject to any disclaimer, the term of this patent is extended or adjusted under 35 U.S.C. 154(b) by 330 days.

(21) Appl. No.: 16/976,348

(22) PCT Filed: Feb. 28, 2019

(86) PCT No.: PCT/EP2019/055059
§ 371 (c)(1),
(2) Date: Aug. 27, 2020

(87) PCT Pub. No.: WO2019/174927
PCT Pub. Date: Sep. 19, 2019

(65) Prior Publication Data
US 2021/0116406 A1    Apr. 22, 2021

(30) Foreign Application Priority Data
Mar. 14, 2018 (EP) .................... 18161786

(51) Int. Cl.
*G01N 27/22* (2006.01)
*G01N 27/12* (2006.01)
*G01N 33/00* (2006.01)

(52) U.S. Cl.
CPC ......... *G01N 27/223* (2013.01); *G01N 27/121* (2013.01); *G01N 33/0031* (2013.01)

(58) Field of Classification Search
CPC . G01N 27/121; G01N 27/223; G01N 33/0031
See application file for complete search history.

(56) References Cited

U.S. PATENT DOCUMENTS 7,222,531 B2    5/2007    Isogai et al.
7,498,823 B2    3/2009    Cerutti
(Continued)

FOREIGN PATENT DOCUMENTS

CN    1782700 A    6/2006
CN    1973200 A    5/2007
(Continued)

OTHER PUBLICATIONS

Sensirion the Sensor Company, "Datasheet SHTC1 Humidity and Temperature Sensor IC," www.sensirion.com, Version 4, Aug. 2015, 14 pages.
(Continued)

*Primary Examiner* — Kristina M Deherrera
*Assistant Examiner* — Jean F Morello
(74) *Attorney, Agent, or Firm* — Slater Matsil, LLP

(57) ABSTRACT

A monolithic sensor arrangement, a manufacturing method and a measurement method are disclosed. In an embodiment a monolithic gas sensor arrangement includes a sensor including a first transducer with a first sensitive layer and a second transducer with a second sensitive layer, and a readout circuit configured to generate a first measurement signal and a second measurement signal depending on the first and second transducers, wherein the sensor arrangement is a humidity sensor arrangement, wherein the first and second sensitive layers are configured to absorb water molecules, and wherein the first and second sensitive layers differ from each other in at least one property.

14 Claims, 9 Drawing Sheets

(56) References Cited

U.S. PATENT DOCUMENTS

| | | | |
|---|---|---|---|
| 9,027,400 | B2 | 5/2015 | Le Neel et al. |
| 9,069,388 | B2 | 6/2015 | Karhiniemi et al. |
| 9,284,187 | B2 | 3/2016 | Daamen et al. |
| 9,287,219 | B2 | 3/2016 | Del Signore et al. |
| 9,417,207 | B2 | 8/2016 | Marra |
| 9,513,245 | B2 * | 12/2016 | Sakai .................. G01N 27/223 |
| 10,274,450 | B2 | 4/2019 | Suy et al. |
| 10,578,573 | B2 | 3/2020 | Zanella, Sr. |
| 10,921,277 | B2 * | 2/2021 | Suy ..................... G01N 27/221 |
| 2004/0075446 | A1 | 4/2004 | Haas |
| 2004/0182153 | A1 * | 9/2004 | Hamamoto .......... G01N 27/225 |
| | | | 73/335.04 |
| 2006/0037393 | A1 * | 2/2006 | Itakura .................. G01D 5/24 |
| | | | 73/335.04 |
| 2006/0096370 | A1 * | 5/2006 | Isogai ................. G01N 27/223 |
| | | | 73/335.04 |
| 2007/0210807 | A1 * | 9/2007 | Arisaka ............... G01N 27/225 |
| | | | 324/664 |
| 2014/0026642 | A1 * | 1/2014 | O'Connell ........... G01N 27/223 |
| | | | 73/31.05 |
| 2014/0125359 | A1 | 5/2014 | El-Gamal et al. |
| 2016/0003770 | A1 | 1/2016 | Klootwijk et al. |
| 2016/0187279 | A1 | 6/2016 | Tayebi et al. |
| 2017/0276627 | A1 | 9/2017 | Dobrokhotov et al. |
| 2018/0180653 | A1 * | 6/2018 | Widdershoven ...... G01L 9/0072 |

FOREIGN PATENT DOCUMENTS

| | | |
|---|---|---|
| CN | 101561427 A | 10/2009 |
| CN | 102203697 A | 9/2011 |
| CN | 103134837 A | 6/2013 |
| CN | 103649738 A | 3/2014 |
| CN | 203519543 U | 4/2014 |
| CN | 104237330 A | 12/2014 |
| CN | 105143869 A | 12/2015 |
| CN | 105319245 A | 2/2016 |
| CN | 105424767 A | 3/2016 |
| CN | 105974062 A | 9/2016 |
| CN | 106796192 A | 5/2017 |
| CN | 106841383 A | 6/2017 |
| EP | 2833129 A1 | 2/2015 |
| EP | 3208610 A1 | 8/2017 |

OTHER PUBLICATIONS

AMS, "ENS210 Relative Humidity and Temperature Sensor with I2C Interface," ams Datasheet, [v1-00], Oct. 24, 2016, 42 pages.

Y. Li, et al., "Monolithic CMOS Multi-Transducer Gas Sensor Microsystem for Organic and Inorganic Analytes," Science Direct, Sensors and Actuators B 126, www.sciencedirect.com, Apr. 5, 2007, 10 pages.

\* cited by examiner

MONOLITHIC SENSOR ARRANGEMENT, MANUFACTURING METHOD AND MEASUREMENT METHOD

This patent application is a national phase filing under section 371 of PCT/EP2019/055059, filed Feb. 28, 2019, which claims the priority of European patent application 18161786.1, filed Mar. 14, 2018, each of which is incorporated herein by reference in its entirety.

TECHNICAL FIELD

The present disclosure relates to a sensor arrangement, a manufacturing method and a measurement method.

SUMMARY

The sensor arrangement may be configured as a chemical sensor arrangement and designed for the measurement of a parameter in a gas or liquid. For example, the sensor arrangement may be realized for the detection of humidity, i.e., for the detection of water molecules in air.

For chemical measurements often capacitive sensors with a sensitive layer are used. For the measurement of parameters in a gas, the sensitive layer is configured to absorb gas molecules. The property of the sensitive layer in such a sensor determines the quality of the measurement.

Embodiments provide an improved concept for a sensor arrangement and a method for generating measurement results which enable an enhanced measurement quality.

The improved concept is based on the idea of a monolithic gas sensor arrangement having multiple transducers with different properties. This arrangement can provide an accurate measurement over a broader range of the gas parameter to be measured compared to a sensor with a single transducer. Alternatively or in addition to enhanced accuracy, a faster accurate measurement can be enabled.

In particular, the improved concept proposes a sensor arrangement having a first transducer with a first sensitive layer and a second transducer with a second sensitive layer, wherein the first and the second sensitive layer differ from each other in at least one property. The monolithic sensor arrangement according to the improved concept further comprises a readout circuit that generates a first measurement signal depending on the capacitance of the first transducer and a second measurement signal depending on the capacitance of the second transducer.

The improved concept further comprises a method for generating a result signal by the readout circuit of such a sensor arrangement depending on the first and the second measurement signal, from which the gas parameter to be measured can be derived.

Various embodiments of the sensor arrangement according to the improved concept are configured to measure relative humidity. In such embodiments the first and the second sensitive layer are of a dielectric material and configured to absorb water molecules from the surrounding gas. The dielectric material of the first and the second sensitive layer can be chosen such that the dielectric constant of water is much higher than that of the dielectric material. Consequently, the measurable change in capacitance is directly proportional to the relative humidity.

For the measurement of the aforementioned capacitance and its change respectively, some implementations may for example comprise interdigitated electrodes of the respective transducer with the sensitive layer in between and in the same plane.

Alternatively to an interdigitated capacitor, in some implementations the electrodes may form a parallel-plate capacitor with the sensitive layer in between the parallel plates.

In various embodiments the first and the second sensitive layer may be of different materials. Dielectric materials for sensitive layers in capacitive gas sensors include polymers, such as polyimides. Different polymers can show non-identical sensitivities in different relative humidity regimes, for example a different absorption behavior. In particular, this means that one polymer could be more sensitive at low relative humidity while the other polymer is more sensitive at high relative humidity. Moreover, the response time of a transducer depends on the diffusion coefficient of the sensitive layer material. Having the first and the second sensitive layer made of different polymers with different diffusion coefficients hence allows for the realization of different response times of the first and the second transducer.

In some embodiments, the first and the second sensitive layer can alternatively or in addition be of different thicknesses. Capacitive transducers can be designed such that their response time is proportional to the thickness of the dielectric material. Choosing different thicknesses for the first and the second sensitive layer allows for a sensor arrangement with the first and the second transducer having different response times.

While having a fast response time, a transducer with a very thin sensitive layer may become susceptible to inaccuracies, for example due to surface contaminations. These inaccuracies occur if electric field lines of the capacitive transducer are no longer fully confined within the sensitive layer. Above a certain threshold of the thickness, the sensitive layer confines the electric field lines, hence enabling accurate measurements.

For the described embodiments, the first transducer can for example be chosen to have a thin layer dielectric material and therefore a fast response time, while the second transducer may possess a thicker sensitive layer and therefore be slower but deliver more accurate results. Depending on the requirements of the application, this allows for simultaneous fast and accurate measurements in contrast to a single transducer sensor, for which a compromise has to be made.

In some embodiments the readout circuit may be configured to generate a result signal as a predefined function of the first and the second measurement signal. Since the first and the second transducer are configured to measure the same quantity, a single result signal may be desired as the output of the readout circuit.

Depending on the properties of the first and the second transducer the readout circuit in such an embodiment may for example apply the predefined function to the first and the second measurement signal in order to give preference to one measurement signal over the other. For example, the predefined function can be a weighted arithmetic mean or comprise filter functions. In such an embodiment, the predefined function can be tailored such to achieve an enhanced measurement result compared to a single-transducer sensor, for example in terms of accuracy and/or measurement rate.

In some embodiments the readout circuit further comprises a memory which stores data that describes the first and the second transducer. For example, the data characterizes accuracy and/or response time of the first and the second transducer depending on relative humidity. The data can hereby either comprise functions or lookup tables.

In such an embodiment the readout circuit generates the result signal from the first and the second measurement signal and the data stored in the memory. For example, the data can be used to convert capacitances into units of relative humidity.

Alternatively or in addition to conversion data, the memory may comprise lookup tables or functions for a first and a second coefficient, $C_1$ and $C_2$. $C_1$ and $C_2$ can for example be used by the readout circuit as weight factors for calculating the weighted arithmetic mean for determining the result signal from the first and the second measurement signal. In particular, for two transducers with for example selective accuracy over the relative humidity range, $C_1$ and $C_2$ depend on relative humidity (RH). Functions or lookup tables for $C_1(RH)$ and $C_2(RH)$ can be obtained by prior characterization measurements of the first and the second transducer and be saved in the memory.

In order for the readout circuit to determine the optimal weight factor $C_1$ and $C_2$ for the generation of the result signal after the first and the second measurement signal have been generated by the readout circuit, a recursive procedure can be applied. First, an equal weight for the first and the second measurement signal, $RH_1$ and $RH_2$, is assumed in order to obtain an initial estimate $RH_{init}$ of the relative humidity, $$RH_{init} = \frac{1}{2}RH_1 + \frac{1}{2}RH_2.$$

Using the initial estimate, an updated and more accurate estimate for the relative humidity RH is obtained via, $$RH = C_1(RH_{init})RH_1 + C_2(RH_{init})RH_2.$$

This process may be repeated multiple times by the readout circuit to further enhance the estimate which is eventually output as the result signal.

This procedure leads to an enhanced accuracy of the relative humidity measurement over the entire range especially if the first and the second transducer are designed for operation in different regimes of the relative humidity range. Hence, this procedure is of particular relevance for embodiments, in which the first and the second sensitive layer differ from each other in terms of the material.

In some embodiments the data stored in the memory comprises a first frequency dependent filter function which is applied to the first measurement signal by the readout circuit and a second frequency dependent filter function which is applied to the second measurement signal by the readout circuit for generating the result signal.

Frequency dependent filter functions may be useful if, for example, the first and the second transducer possess different polymer thicknesses. In such an embodiment an accurate measurement of the relative humidity can be obtained from the transducer with the thicker polymer, while the transducer with the thinner polymer has a larger bandwidth, i.e., response rate, and therefore is able to follow fast changes in relative humidity. A combination of both measurement signals using appropriate filter functions enables fast and accurate relative humidity measurements. The first and the second filter function can be obtained by prior characterization measurements of the first and the second transducer and be saved in the memory.

The same procedure can be applied to the first and the second transducer to account for measurement uncertainties, such as for example drift, which typically is limited to low-frequency components in the measurement signal.

For example, the first transducer may have a smaller drift compared to the second transducer but a larger noise component, which is usually a white noise, i.e., has a constant power spectral density with respect to frequency. In this case for the generation of the result signal the readout circuit applies the first and the second filter function as to put more weight on low-frequency components from the first transducer and accordingly more weight on high-frequency components from the second transducer.

The aforementioned object is further solved by a method of manufacturing a monolithic gas sensor arrangement.

The method comprises manufacturing a first transducer on a substrate with the first transducer comprising a first sensitive layer. The method further comprises manufacturing a second transducer on the substrate with the second transducer comprising a second sensitive layer. The first and the second sensitive layer are characterized in that they differ from each other in at least one property.

The differing property of the first and the second sensitive layer may for example be the thickness and/or the material.

The method may further comprise manufacturing a readout circuit on the substrate, with the readout circuit being configured to generate measurement signals based on the first and the second transducer.

The aforementioned object is further solved by a method of generating a result signal from a capacitive gas sensor arrangement having a first transducer with a first sensitive layer and a second transducer with a second sensitive layer, wherein the first and the second sensitive layer differ from each other in at least one property.

The method comprises the generation of a first and second measurement signal based on the capacitance of the respective transducer and generating a result signal by application of a predefined function, for example by a readout circuit.

In some embodiments the method may utilize a memory that stores data characterizing the first and the second transducer. This characterization data may for example describe the measurement-dependent and/or frequency-dependent sensitivities of the first and the second transducer. This data can be used to generate the result signal.

In an embodiment the data stored in the memory comprises weight factors used to determine a weighted arithmetic mean of the first and the second measurement signal and generate the result signal from this weighted arithmetic mean.

For example, if the first and the second transducer possess different selective accuracies across the measurement range, a weighted arithmetic mean may enable a more accurate measurement over a broader range compared to a single-transducer measurement.

Alternatively or in addition, the data in the memory may comprise a first and a second frequency-dependent filter function used to generate the result signal.

For example, if the first and the second transducer have different measurement response rates, filter functions allow combining the first and the second measurement signal in order to achieve an enhanced accuracy at a higher measurement rate compared to a single-transducer measurement.

Further embodiments of the methods become apparent to the skilled person from the embodiments of the sensor arrangement described above.

BRIEF DESCRIPTION OF THE DRAWINGS

The following description of figures of example embodiments may further illustrate and explain aspects of the improved concept. Devices and circuit parts with the same structure and the same effect, respectively, appear with equivalent reference symbols. In so far as devices or circuit parts correspond to one another in terms of their function in different figures, the description thereof is not repeated for each of the following figures.

DETAILED DESCRIPTION OF ILLUSTRATIVE EMBODIMENTS

Figure 1A:
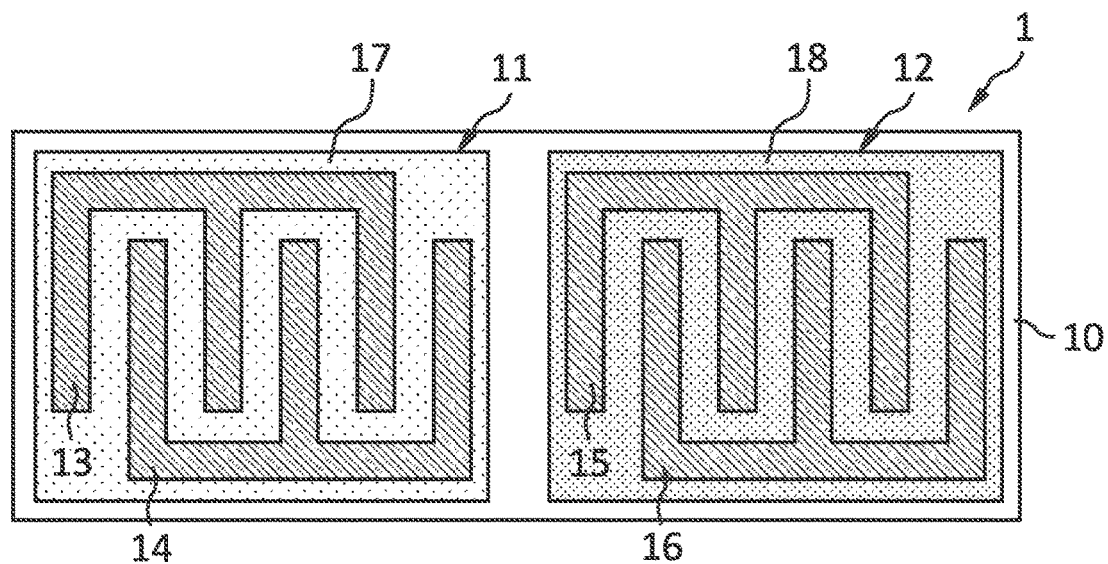
FIGS. 1A to 1C show exemplary embodiments of a sensor arrangement with two capacitive transducers according to the improved concept.

FIG. 1A shows an exemplary embodiment of a monolithic sensor arrangement 1 comprising a first transducer 11 and a second transducer 12 on a substrate 10. The first transducer 11 comprises a first electrode line 13 and a second electrode line 14. The first and the second electrode line 13, 14 are arranged inside a first sensitive layer 17 in an interdigitated manner. The second transducer 12 comprises a third electrode line 15 and a fourth electrode line 16. The third and the fourth electrode line 15, 16 are arranged inside a second sensitive layer 18 in an interdigitated manner. The first and the second sensitive layer 17, 18 may be a dielectric, such as a polymer. In particular, the first and the second sensitive layer 17, 18 may be of different materials.

Figure 1B:
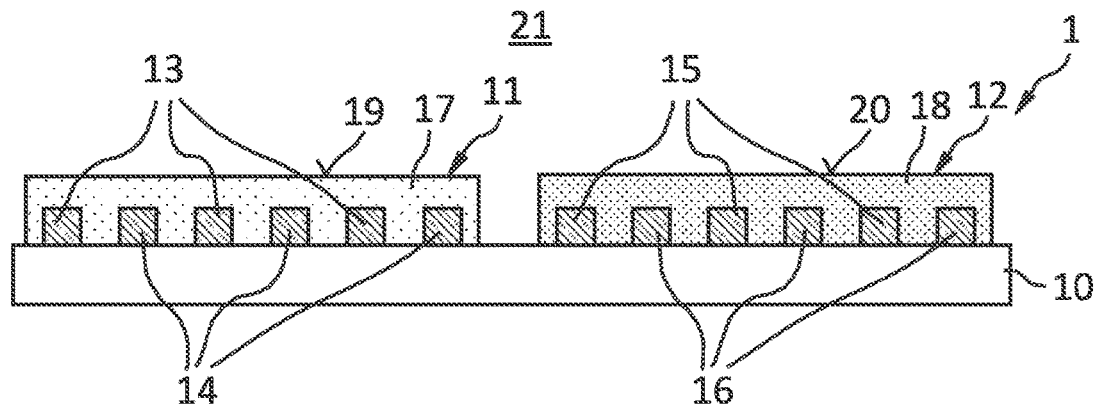

FIG. 1B shows the cross-section of the exemplary embodiments shown in FIG. 1A. The first and the second electrode line 13, 14 of the first transducer 11 are surrounded by the first sensitive layer 17. The third and the fourth electrode line 15, 16 of the second transducer 12 are surrounded by the second sensitive layer 18. The first sensitive layer 17 has an interface 19 to an ambient gas 21. The second sensitive layer 18 has an interface 20 to the ambient gas 21. The ambient gas 21 comprises the parameter to be detected, such as water molecules, i.e., relative humidity, or another target gas.

The first and the second electrode line 13 and 14 of the first transducer 11 form in this embodiment an interdigitated capacitor. For relative humidity detection the polymers 17 and 18 are configured to absorb water molecules from the ambient gas 21 via the interfaces 19 and 20. To this end, the materials possess dielectric constants significantly lower than that of water. Upon absorption, the dielectric properties, i.e., the effective dielectric constant, of the first and the second sensitive layer 17 and 18 are modified. This causes the measured capacitances between the first and the second electrode line 13 and 14 of the first transducer 11 and between the third and the fourth electrode line 15 and 16 of the second transducer 12 to change in a detectable manner. The changes in capacitance are in this embodiment proportional to the relative humidity of the ambient gas 21.

Figure 2A:
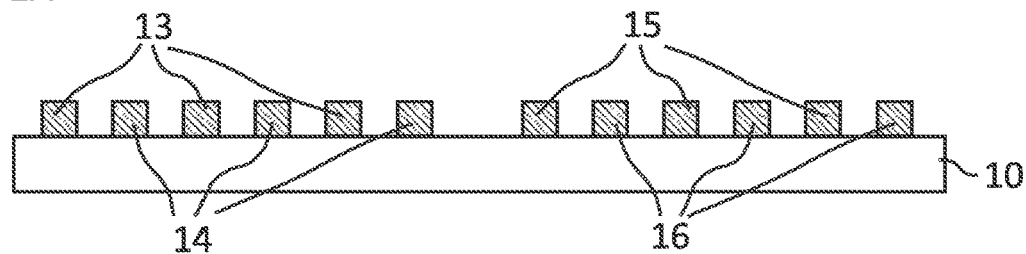
FIGS. 2A to 2E show example steps of a manufacturing method of the embodiment shown in FIGS. 1A and 1B.
Figure 2B:
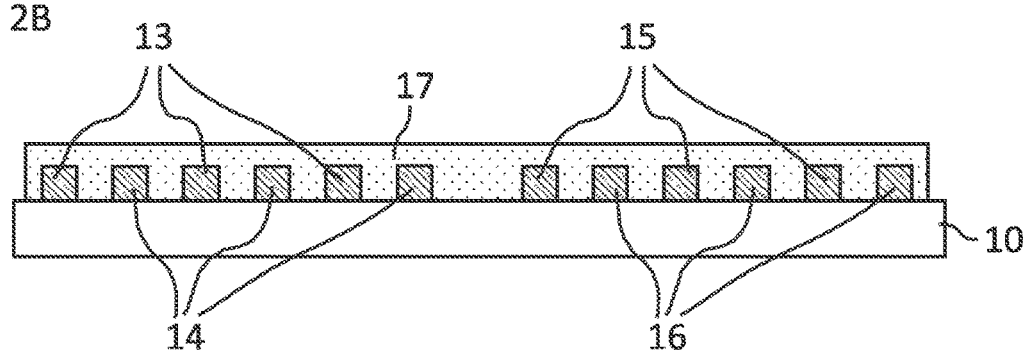
Figure 2C:
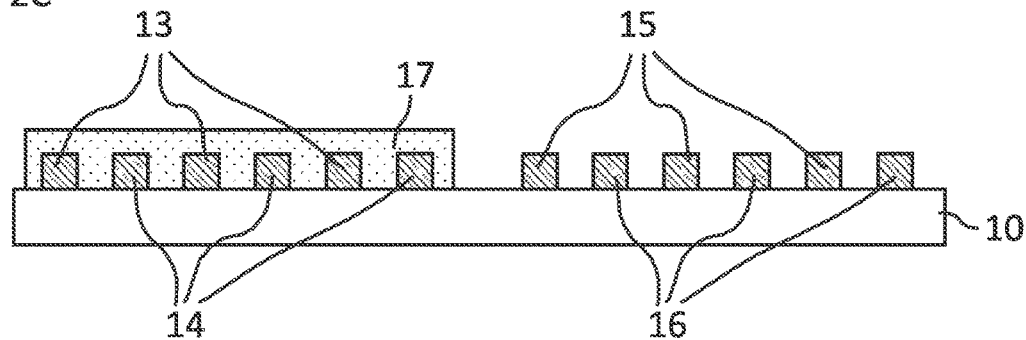
Figure 2D:
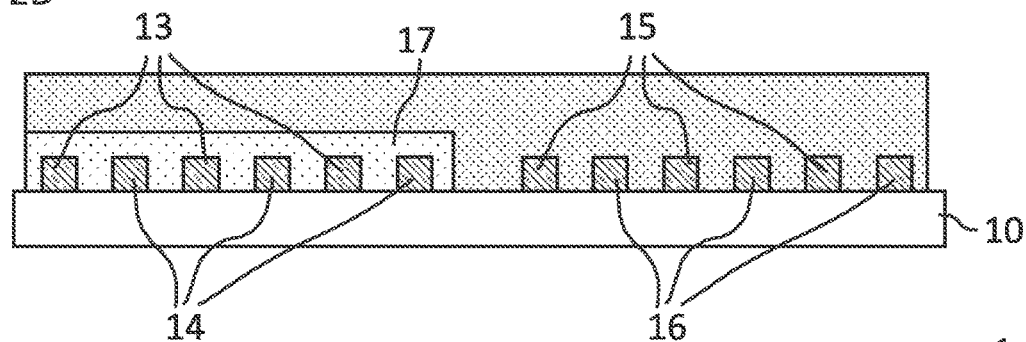
Figure 2E:
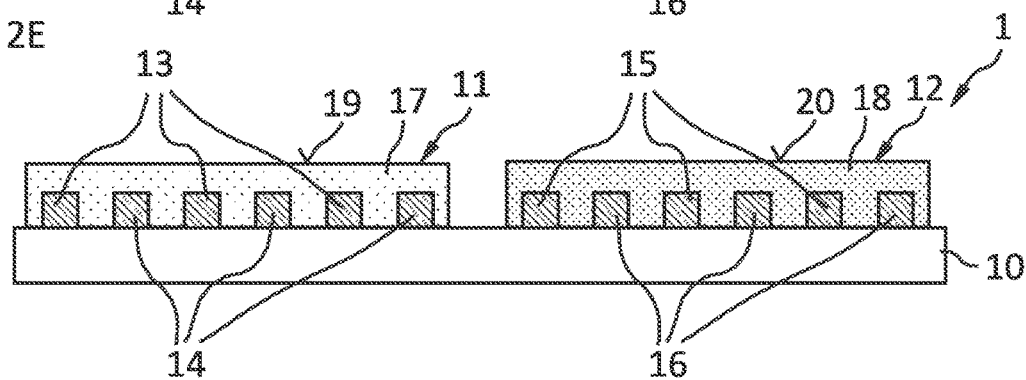

FIGS. 2A to 2E show example steps of a manufacturing method of this embodiment. After realization of the interdigitated electrode lines 13 to 16 on the substrate 10 (FIG. 2A), a first material is applied (FIG. 2B) and structured (FIG. 2C) to form the first sensitive layer 17 embedding the first and the second electrode line 13, 14. Afterwards, a second material is applied (FIG. 2D) and structured (FIG. 2E), forming the second sensitive layer 18 embedding the third and the fourth electrode line 15, 16, as illustrated in FIGS. 2D and 2E.

Figure 1C:
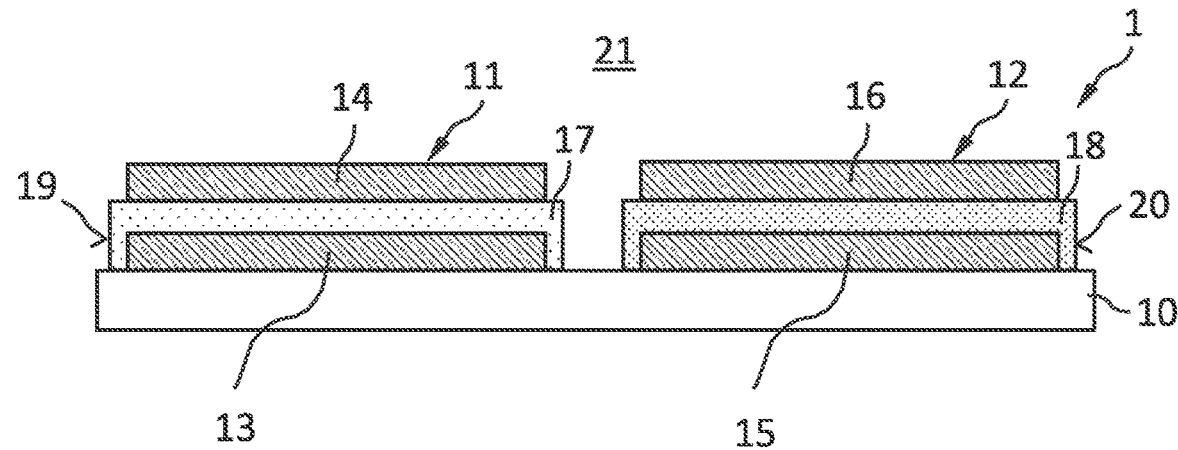

Alternatively to the example of an interdigitated capacitor described above, another exemplary embodiment of the sensor arrangement 1 comprises parallel-plate capacitors as the first and second transducer, as shown in FIG. 1C. In this setup, two parallel plate electrodes form the respective capacitor with a dielectric material, such as a polymer, in between the electrodes.

For the manufacturing of this embodiment, after realization of the first and the third electrode line 13, 15 on the substrate 10, a first material is applied and structured to form the first sensitive layer 17. Afterwards, a second material forming the second sensitive layer 18 is applied and structured. Finally, the second and the fourth electrode line 14, 16 are applied and structured to finalize the first and the second parallel-plate transducer 11, 12.

As materials show different proportionalities of the effective dielectric constant across the relative humidity range, in the exemplary embodiments illustrated in FIGS. 1A to 1C, two different dielectrics are employed as the first and the second sensitive layer 17 and 18. For example, these two materials can be configured such that they possess their peak sensitivities in different regimes of relative humidity, respectively. Using these embodiment accurate measurements across a broader humidity range can be achieved.

Figure 3A:
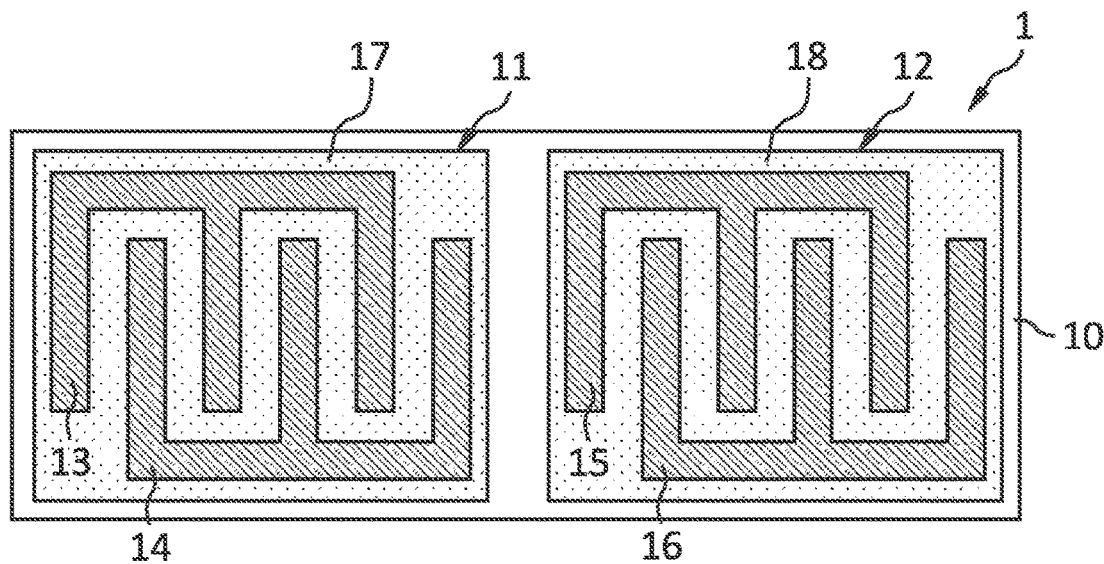
FIGS. 3A to 3C show a further exemplary embodiment of a sensor arrangement with two capacitive transducers according to the improved concept.
Figure 3B:
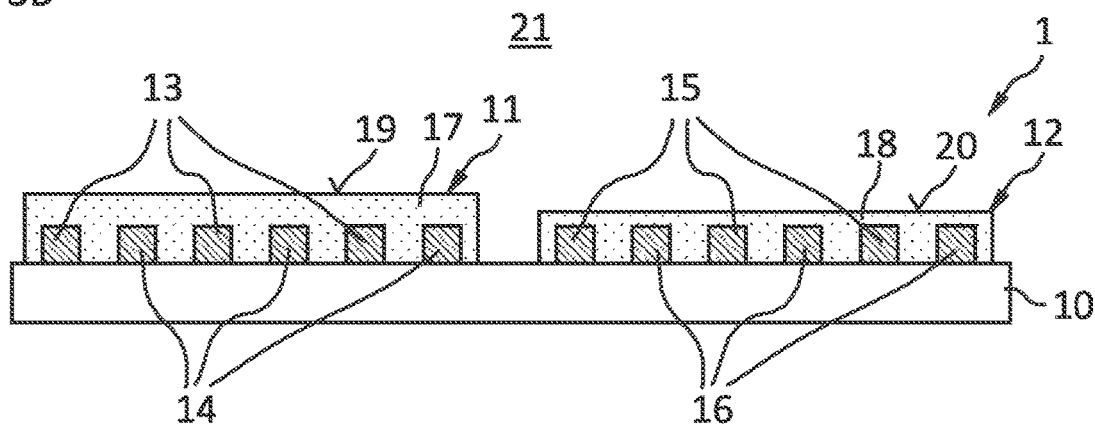

In an alternative embodiment the first and the second sensitive layer 17, 18 may be of the same dielectric material but with different thicknesses, as shown in FIGS. 3A and 3B for an interdigitated electrode layout.

FIGS. 4A to 4D show example steps of a manufacturing method of this embodiment. After realization of the interdigitated electrode lines 13 to 16 on the substrate 10 (FIG. 4A), a dielectric material is applied (FIG. 4B) and structured (FIG. 4C) to form a first part of the first sensitive layer 17 embedding the first and the third electrode line 13, 14. Afterwards, the same dielectric material is applied and structured again (FIG. 4D) to form both the second sensitive layer 18 surrounding the third and the fourth electrode line 15, 16 and a second part of the first sensitive layer 17.

Figure 3C:
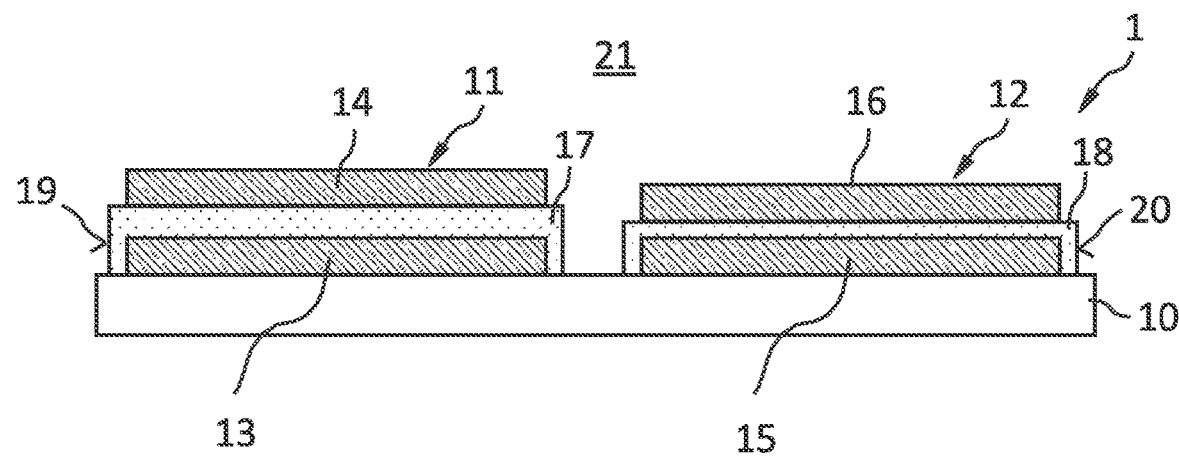
Figure 4A:
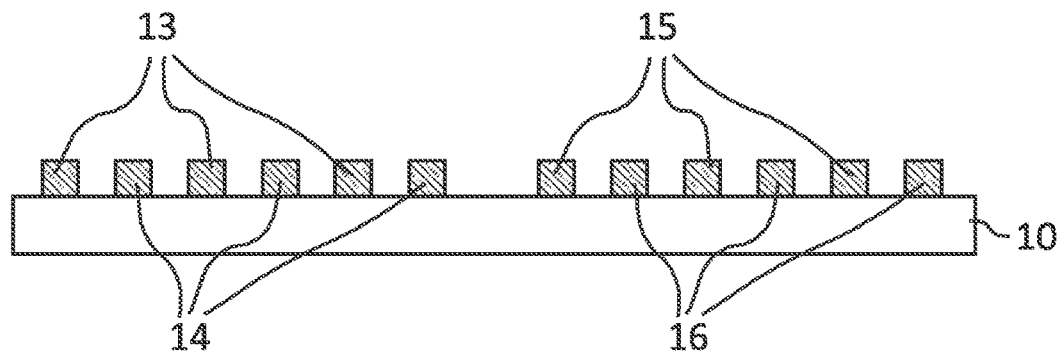
FIGS. 4A to 4D show example steps of a manufacturing method of the embodiment shown in FIGS. 3A and 3B.
Figure 4B:
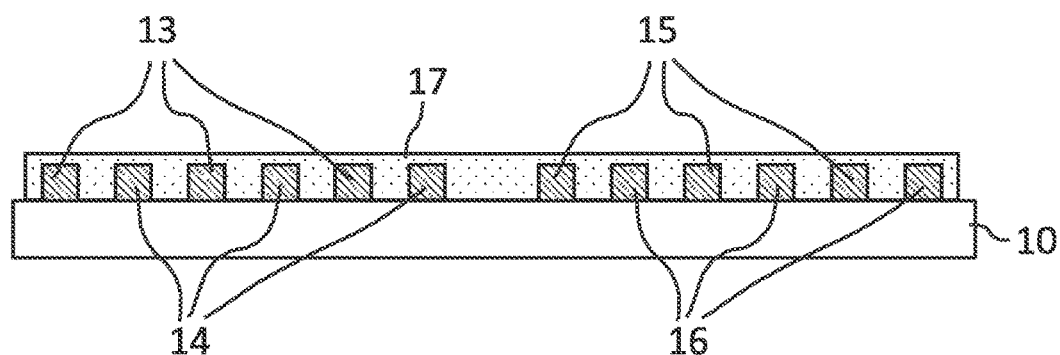
Figure 4C:
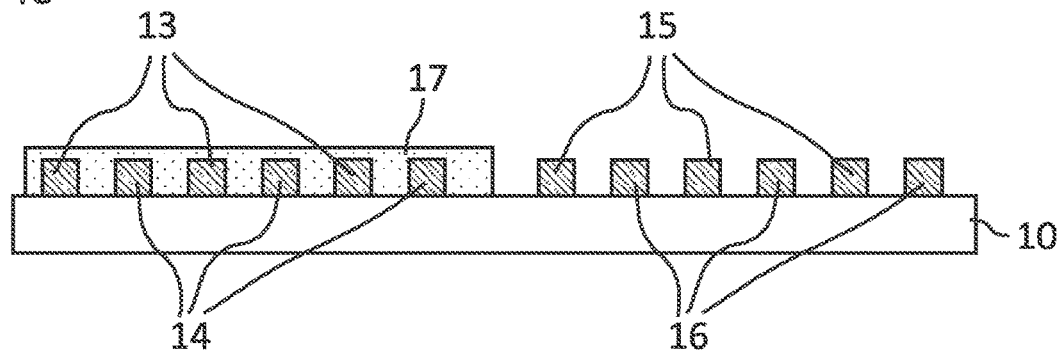
Figure 4D:
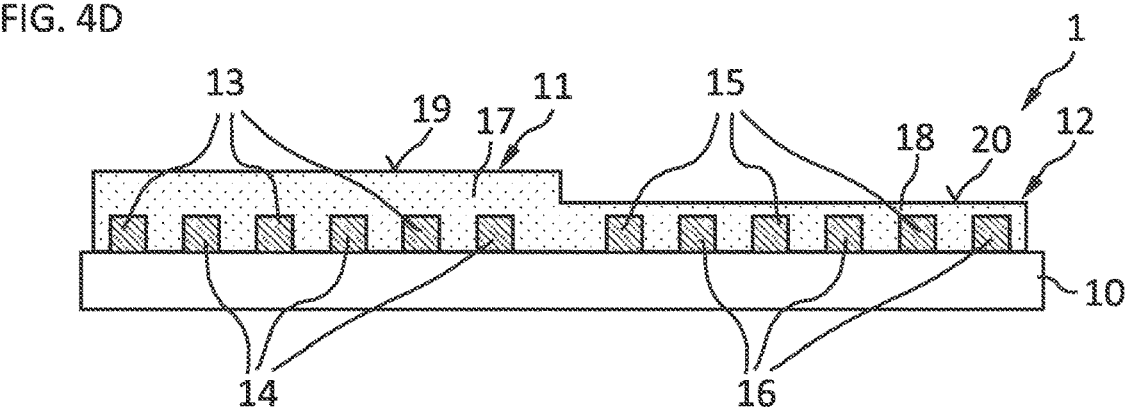

Analogous to the example described in FIG. 1C, a parallel-plate capacitor design is also possible for an embodiment with different thicknesses, as shown in FIG. 3C. The manufacturing steps for the parallel-plate design follow from the example described and shown in FIG. 1C.

The response time of a capacitive transducer is proportional to its thickness. This means that the thinner a sensitive layer in a capacitive transducer is, the better it can follow fast changes in relative humidity. The lower boundary for the thickness of a sensitive layer is hereby given by the point at which electric field lines of the electrodes begin to lose confinement by the sensitive layer. In this case a measurement of the capacitance becomes susceptible to surface effects as source of error. For example, a typical dimension for the thickness of the thin sensitive layer in the described embodiment is in the order of a few micrometers, allowing measurements of the capacitance with sufficient accuracy with measurement times of approximately 200 ms. This is significantly shorter than changes in relative humidity typically occur.

For example, a sensor arrangement 1 may comprise the first transducer 11 having a standard thickness polymer as sensitive layer 17, e.g., several micrometers, e.g., 4-5 micrometers thick, while the second sensitive layer 18 is significantly thinner, for example less than 3 micrometers. Consequently, a measurement of the first transducer 11 yields a high-accuracy measurement of the relative humidity, while a fast measurement of the second transducer 12 enables to track fast changes of this quantity.

Figure 5:
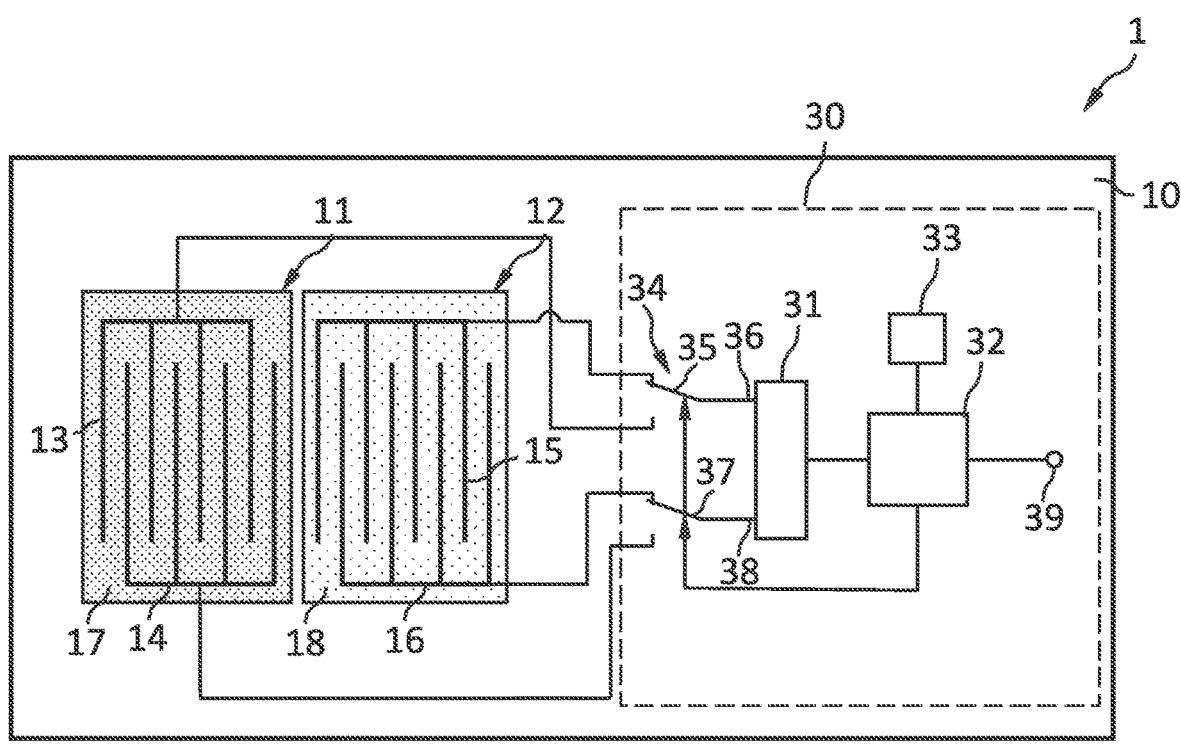
FIG. 5 shows an embodiment of a sensor arrangement including a readout circuit according to the improved concept.

FIG. 5 shows a monolithic sensor arrangement comprising a first and a second capacitive transducer 11, 12 and a readout circuit 30 on a substrate 10, for example a chip substrate. The readout circuit 30 is electrically coupled to the first electrode line 13, the second electrode line 14, the third electrode line 15 and the fourth electrode line 16. The readout circuit 30 comprises a capacitance-to-digital converter 31, abbreviated converter. The converter 31 is electrically coupled to the first, second, third and fourth electrode lines 13 to 16. The readout circuit 30 further comprises a digital processor 32 that is coupled on its input side to the converter 31. The readout circuit 30 further comprises a memory 33 that is coupled to the digital processor 32. Furthermore, the readout circuit 30 comprises a switching arrangement 34. A control input of the switching arrangement 34 is coupled to an output of the digital processor 32. The switching arrangement 34 comprises a first changeover switch 35 having a first input connected to the first electrode line 13, a second input connected to the third electrode line 15 and an output connected to a first input 36 of the converter 31. Furthermore, the switching arrangement 34 comprises a second changeover switch 37 with a first input connected to the second electrode line 14, a second input connected to the fourth electrode line 16 and an output connected to a second input 38 of the converter 31.

In a first phase of a measurement process, the first electrode line 13 is coupled to the first input 36 of the converter 31 via the first changeover switch 35, while the second electrode line 14 is coupled to the second input 38 of the converter 31 via the second changeover switch 37. The converter 31 generates a first measurement signal, which is a function of the capacitance between the first electrode line 13 and the second electrode line 14. In a second phase of the measurement, the third electrode line 15 is coupled via the first changeover switch 35 to the first input 36 of the converter 31, while the fourth electrode line 16 is coupled to the second input 38 of the converter 31 via the second changeover switch 37. The converter 31 generates a second measurement signal, which is a function of the capacitance between the third electrode line 15 and the fourth electrode line 16. The first and the second measurement signal are provided to the digital processor 32.

In an alternative embodiment not shown, the output of the second changeover switch 37 is connected to a reference potential terminal.

In an alternative embodiment not shown, the second and the fourth electrode lines 14, 16 are directly connected to a reference potential terminal. The second changeover switch 37 in such an embodiment is omitted.

The digital processor 32 generates a result signal at an output 39. The result signal may be realized as a humidity signal. The humidity signal provides information about the relative humidity in the ambient gas 21. The result signal is determined by the digital processor 32 using the first and the second measurement signal and data stored in the memory 33. The memory 33 may store parameters of functions or a lookup table which are used for the calculation of the result signal using the first and the second measurement signal as inputs. The parameter of the functions or lookup table may be stored in a non-volatile block of the memory 33 such as an electrically erasable programmable read-only memory, abbreviated EEPROM, or a one-time programmable memory, abbreviated OTP.

In the above described case of the readout circuit 30 comprising a switching arrangement 34, the first and the second measurement signal are generated in separate phases, as described above. This implies that they are generated at separate points in time and the digital processor 32 may be in this case configured to store intermediate values, for example the first and the second measurement signal, in a volatile block of the memory 33.

Since measurement times of capacitive transducers are short, for example in the order of 100-200 ms as described above, compared to typical changes in relative humidity, the alternating generation of the first and the second measurement signal is sufficient in this embodiment. Typical changes in relative humidity occur on the timescale of multiple seconds.

In an embodiment not shown, the readout circuit is configured to generate the first and the second measurement signal simultaneously.

The result signal can for example be a weighted arithmetic mean with the weight factors stored in the memory 33. This method is employed in particular for the embodiment described in FIGS. 1A to 1C, in which different materials for the first and the second sensitive layer 17, 18 are used in order to design the first and the second transducer 11, 12 to have a selective accuracy for certain relative humidity regimes. For example, the first transducer 11 may be designed to be sensitive at high relative humidity, while the second transducer 12 may be sensitive at low relative humidity, as shown in FIGS. 6A and 6B.

Figure 6A:
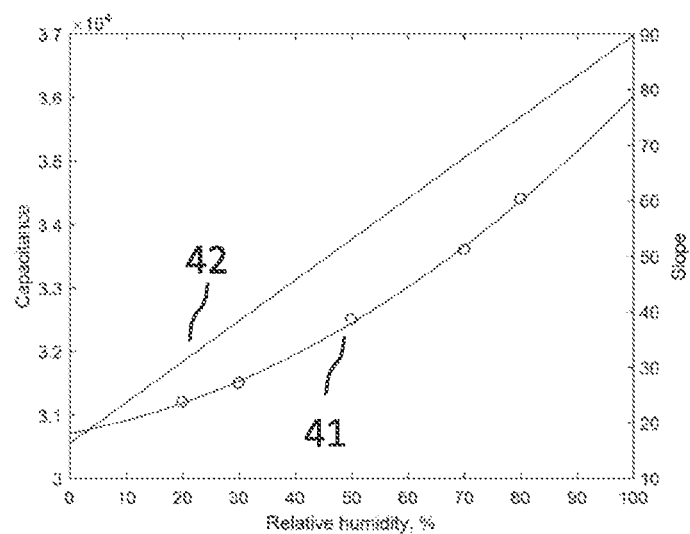
FIGS. 6A and 6B show sensitivities of two exemplary transducers according to the improved concept.
Figure 6B:
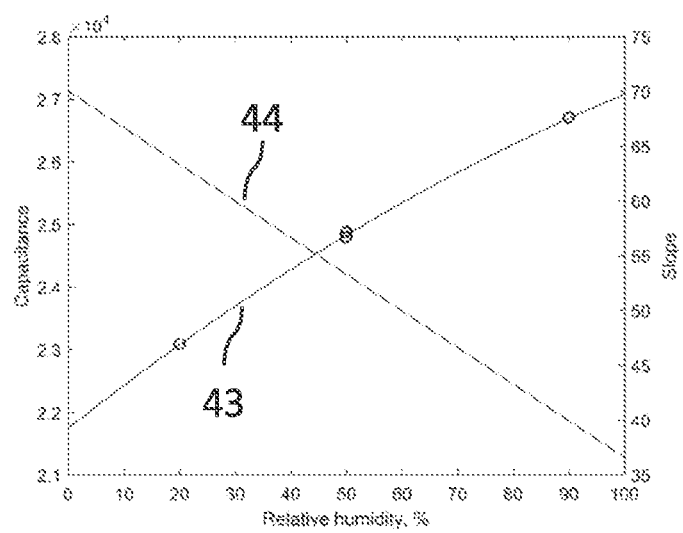

FIG. 6A shows the measurement (circles) of the capacitance of a first exemplary transducer 11 with respect to relative humidity together with a fit 41 (solid line). From this fit the slope 42 of the capacitance behavior is obtained via derivation, representing the sensitivity of the first transducer 11. In this example, the first transducer 11 is more sensitive at high relative humidity. An analogous measurement of an exemplary second transducer 12 is shown in FIG. 6B as the capacitance versus relative humidity 43 and its slope 44. In contrast to the first transducer 11, the second transducer 12 is in this case more sensitive at low relative humidity.

Figure 7A:
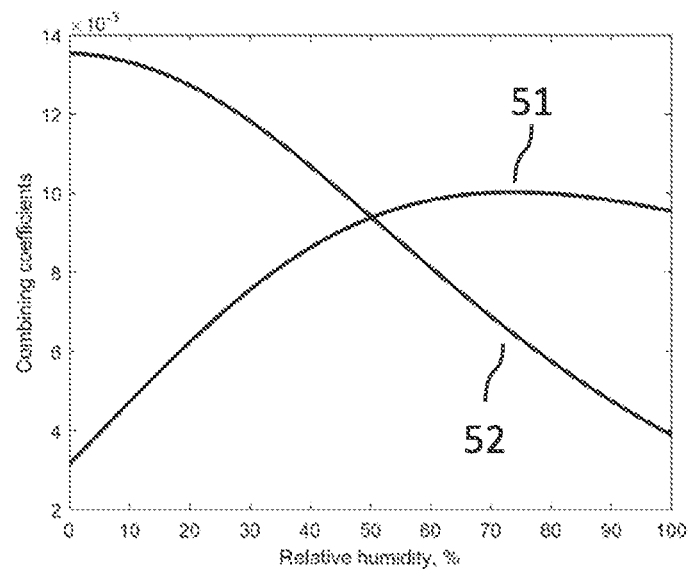
FIGS. 7A and 7B show means for calculating a result signal from the two exemplary transducers of FIGS. 6A and 6B.

FIG. 7A shows combining coefficients, i.e., weight factors, determined from the above mentioned measurement. The lines show the coefficients 51, 52 determined for the respective transducer 11, 12. With these coefficients the result signal can be calculated as a weighted arithmetic mean from the first and the second measurement signal by the digital processor 32 in order to maximize the signal-to-noise ratio of a relative humidity measurement.

Figure 7B:
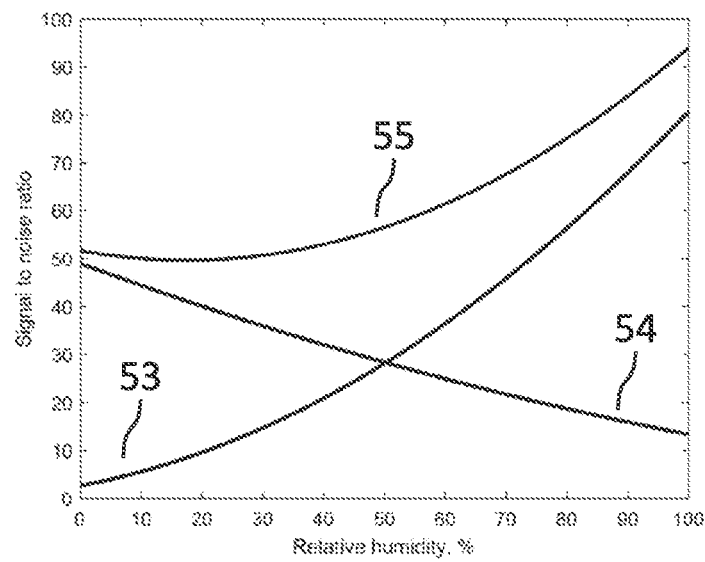

FIG. 7B shows the resulting accuracy 53, 54 in terms of the signal-to-noise ratio (SNR) of the first and the second transducer 11, 12 and the SNR 55 after combining the first and the second measurement signal by a weighted arithmetic mean. The SNR of the result signal is larger than that of the first and the second measurement signal over the entire relative humidity range. In particular, around a relative humidity level of 50%, the gain in SNR is in this example a factor of 2.

In some embodiments, the result signal is generated by the digital processor 32 with the focus on compensating differences in drift properties and/or noise properties. In this case the data in the memory 33 may comprise a lookup table or parameters for a first and a second filter function.

Figure 8A:
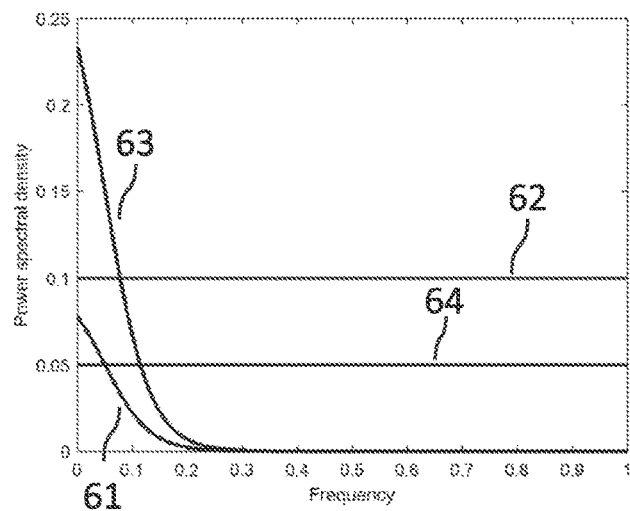
FIGS. 8A to 8C show a frequency-dependent analysis of two exemplary transducers according to the improved concept.

FIG. 8A shows typical exemplary noise properties and drift properties of a first and a second transducer 11, 12 with respect to frequency. In particular, the drifts versus frequency 61 and 63 of the respective transducer 11, 12 and their noise versus frequency 62, 64 are shown. Typically, drifts of capacitive transducers only occur at low rates, i.e., low frequencies, while they are susceptible to white noise that is independent of frequency.

Figure 8B:
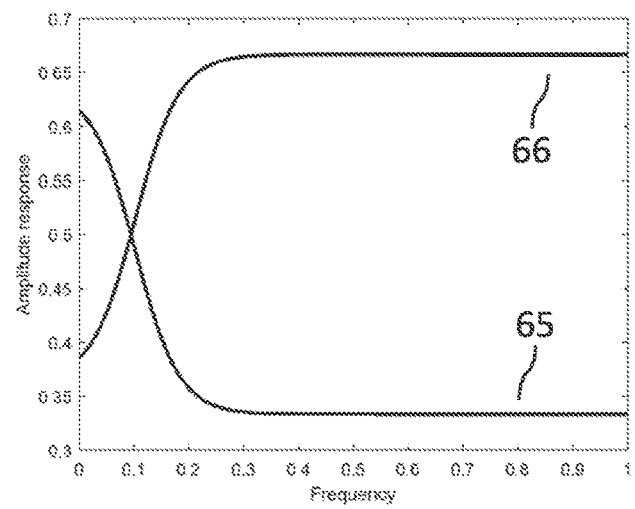

Following the properties of the exemplary first and second transducer 11, 12, the first and the second filter functions are determined in order to maximize the signal-to-noise ratio with respect to frequency. FIG. 8B shows the determined first and second filter function 65 and 66 for the respective transducer. Owing to its smaller drift, the first transducer 11 is preferred at low frequencies, while the second transducer 12 gives the better result at high frequencies due to its lower noise.

Figure 8C:
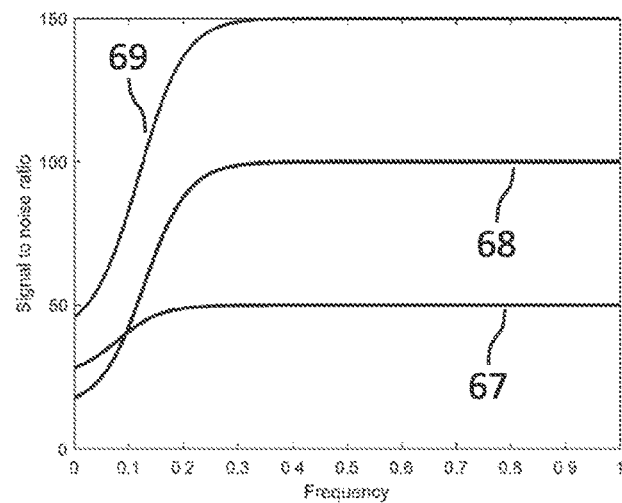

FIG. 8C shows the SNR 67 and 68 of the respective transducer with respect to frequency and the resulting SNR 69 after generating the result signal by applying the first and the second filter function.

In an alternative embodiment, in particular of that kind described in FIGS. 3A to 3C, where different thicknesses of the polymer are employed as the first and the second sensitive layer 17, 18, the first and the second filter function can be applied to the first and the second measurement signal, respectively, to generate the result signal by the digital processor 32.

In such an embodiment, the first transducer 11 can for example have a standard thickness polymer as the first sensitive layer 17 and hence provide accurate measurements but at limited bandwidth, while the second transducer 12 may have a thin polymer as sensitive layer 18 and provide fast measurements, i.e., be able to follow quick changes in relative humidity.

Figure 9:
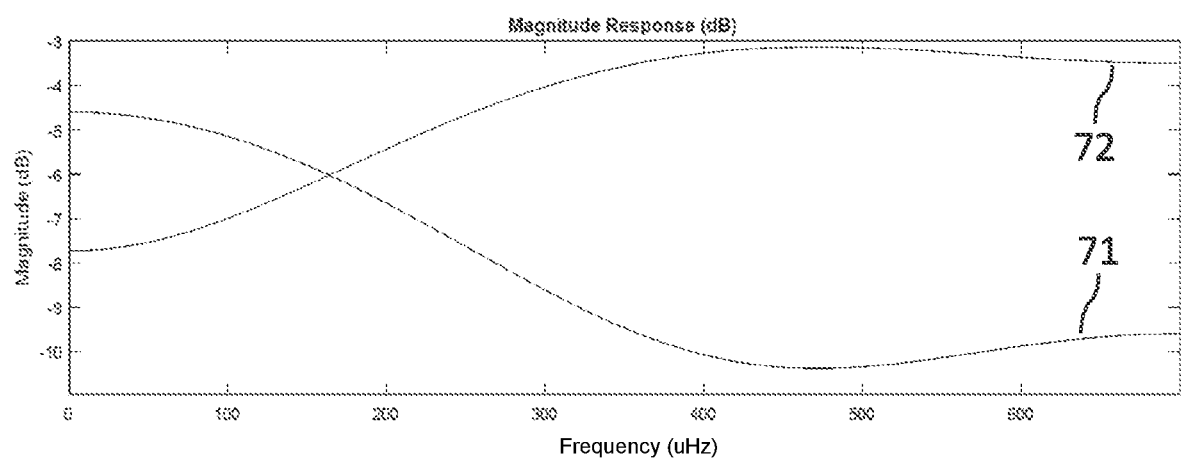
FIG. 9 shows generated filter functions for exemplary transducers of FIGS. 8A and 8B.

FIG. 9 shows an example of the first and the second filter function 71 and 72 for the respective transducer determined for such an embodiment with the aim of increasing the SNR of the result signal across frequencies of relevance. This procedure is analogous to the case described above, in which the drift and noise properties of the first and second transducer 11, 12 are accounted for.

The invention claimed is:

1. A monolithic gas sensor arrangement comprising:
a sensor comprising:
a first transducer with a first sensitive layer; and
a second transducer with a second sensitive layer
wherein the first and second sensitive layers are configured to absorb water molecules, and
wherein the first and second sensitive layers differ from each other in at least one property; and
a readout circuit comprising a memory,
wherein the readout circuit is configured to:
generate a first measurement signal and a second measurement signal depending on the first and second transducers, and
provide a result signal as a pre-defined function of the first and second measurement signals and data stored in the memory,
wherein the data stored in the memory comprise weight factors that are functions of the first and/or second measurement signals,
wherein the weight factors are usable to generate the result signal as a weighted mean of the first and second measurement signals,
wherein an equal weight for the first and second measurement signals $RH_1$, $RH_2$ is provided in order to obtain an initial estimate $RH_{init}$ of a relative humidity, wherein the initial estimate is $$RH_{init} = \tfrac{1}{2}RH_1 + \tfrac{1}{2}RH_2,$$

wherein, based on the initial estimate $RH_{init}$, an updated estimate for the relative humidity RH is obtained via the equation:

$$RH = C_1(RH_{init})RH_1 + C_2(RH_{init})RH_2,$$

wherein $C_1(RH_{init})$ is a first coefficient that depends on the initial estimate,
wherein $C_2(RH_{init})$ is a second coefficient that depends on the initial estimate, and
wherein the sensor arrangement is a humidity sensor arrangement.

2. The sensor arrangement according to claim 1, wherein the first and second sensitive layers are of different materials.

3. The sensor arrangement according to claim 1, wherein the first and second sensitive layers are of different thicknesses.

4. The sensor arrangement according to claim 1, wherein the first and second transducers differ from each other in accuracy and/or sensitivity.

5. The sensor arrangement according to claim 1, wherein the first and second transducers are configured such that they differ from each other in response rate.

6. The sensor arrangement according to claim 1, wherein the data stored in the memory comprise a first filter function and a second filter function, and wherein the first and second filter function are configured to be applied to the first and second measurement signals to generate the result signal.

7. The sensor arrangement according to claim 6, wherein the first and second filter function depend on noise properties and/or drift properties of the first and second transducers.

8. The sensor arrangement according to claim 1, wherein the first and second transducers are arranged on a substrate.

9. The sensor arrangement according to claim 1, wherein the first and the second transducer are capacitors.

10. The sensor arrangement according to claim 9, wherein the first and second transducers are interdigitated capacitors.

11. The sensor arrangement according to claim 9, wherein the first and second transducers are parallel-plate capacitors.

12. A method for manufacturing a monolithic gas sensor arrangement, the method comprising:
manufacturing a first transducer on a substrate, the first transducer comprising a first sensitive layer;
manufacturing a second transducer on the substrate, the second transducer comprising a second sensitive layer,
wherein the first and second sensitive layers are manufactured for absorbing water molecules, and
wherein the first and second sensitive layers differ from each other in at least one property; and
providing a readout circuit comprising a memory,
wherein the readout circuit is configured for providing a result signal as a pre-defined function of a first measurement signal, a second measurement signal and data stored in the memory,
wherein the data stored in the memory comprise weight factors that are functions of the first and/or second measurement signals, wherein the weight factors are usable to generate the result signal as a weighted mean of the first and second measurement signals, wherein an equal weight for the first and second measurement signals $RH_1$, $RH_2$ is provided in order to obtain an initial estimate $RH_{init}$ of a relative humidity, wherein the initial estimate is $$RH_{init} = \tfrac{1}{2}RH_1 + \tfrac{1}{2}RH_2,$$

wherein, based on the initial estimate $RH_{init}$, an updated estimate for the relative humidity RH is obtained via the equation:

$$RH = C_1(RH_{init})RH_1 + C_2(RH_{init})RH_2,$$

wherein $C_1$ ($RH_{init}$) is a first coefficient that depends on the initial estimate, wherein $C_2$ ($RH_{init}$) is a second coefficient that depends on the initial estimate, and wherein the sensor arrangement is a humidity sensor arrangement.

13. A method for generating a result signal from a capacitive gas sensor arrangement having a first transducer with a first sensitive layer and a second transducer with a second sensitive layer, wherein the sensor arrangement is a humidity sensor arrangement, and wherein the first and second sensitive layers differ from each other in at least one property, the method comprising:

absorbing, by the first and second sensitive layers, water molecules;

generating, by the first transducer, a first measurement signal;

generating, by the second transducer, a second measurement signal; and generating the result signal as a pre-defined function of the first and second measurement signals and data stored in a memory, wherein the data comprise weight factors and the result signal is a weighted mean of the first and second measurement signals of the weight factors, wherein an equal weight for the first and second measurement signals $RH_1$, $RH_2$ is provided in order to obtain an initial estimate $RH_{init}$ of a relative humidity, wherein the initial estimate is $$RH_{init} = \tfrac{1}{2}RH_1 + \tfrac{1}{2}RH_2,$$

wherein, using the initial estimate $RH_{init}$, an updated estimate for the relative humidity RH is obtained via the equation:

$$RH = C_1(RH_{init})RH_1 + C_2(RH_{init})RH_2,$$

wherein $C_1$ ($RH_{init}$) is a first coefficient that depends on the initial estimate, and wherein $C_2$ ($RH_{init}$) is a second coefficient that depends on the initial estimate.

14. The method according to claim 13, wherein the data comprise a first filter function and a second filter function and the result signal is generated by applying the first filter function to the first measurement signal and the second filter function to the second measurement signal.

* * * * *